United States Patent [19]

Hirsch et al.

[11] Patent Number: 5,345,935
[45] Date of Patent: Sep. 13, 1994

[54] NON-INVASIVE MEDICAL PROBE PROVIDED WITH SUCTION CUP

[75] Inventors: Harold D. Hirsch, Taunton; John A. D. Spencer, Pinner, both of United Kingdom; Ilan Z. Samson, Tel Aviv, Israel

[73] Assignee: Egnell Ameda Limited, Somerset, United Kingdom

[21] Appl. No.: 937,874
[22] PCT Filed: Apr. 19, 1991
[86] PCT No.: PCT/GB91/00615
 § 371 Date: Oct. 16, 1992
 § 102(e) Date: Oct. 16, 1992
[87] PCT Pub. No.: WO91/15996
 PCT Pub. Date: Oct. 31, 1991

[30] Foreign Application Priority Data

Apr. 19, 1990 [GB] United Kingdom ............... 9008764

[51] Int. Cl.⁵ ............................................. A61B 5/0448
[52] U.S. Cl. .................... 128/642; 128/643; 128/633; 128/635; 128/662.03; 128/736
[58] Field of Search .............. 128/642, 643, 633, 635, 128/662.03, 736

[56] References Cited

U.S. PATENT DOCUMENTS

| 3,490,442 | 1/1970 | Steu . | |
|---|---|---|---|
| 3,505,993 | 4/1970 | Lewes et al. | 128/643 |
| 3,534,733 | 10/1970 | Phipps et al. | 128/643 |
| 3,958,564 | 5/1976 | Langguth . | |
| 4,217,908 | 8/1980 | Staver . | |
| 4,299,232 | 11/1981 | Zilianti | 128/643 |
| 4,308,873 | 1/1982 | Maynard | 128/643 X |
| 4,369,793 | 1/1983 | Staver et al. . | |
| 4,537,197 | 8/1985 | Hulka . | |
| 4,736,749 | 4/1988 | Lundback . | |
| 4,878,900 | 11/1989 | Sundt . | |

FOREIGN PATENT DOCUMENTS

| 0135840 | 3/1985 | European Pat. Off. . | |
|---|---|---|---|
| 332212 | 1/1921 | Fed. Rep. of Germany . | |
| 1655803 | 4/1953 | Fed. Rep. of Germany . | |
| 2742058 | 3/1979 | Fed. Rep. of Germany . | |
| 2749048 | 5/1979 | Fed. Rep. of Germany . | |
| 2830412 | 1/1980 | Fed. Rep. of Germany . | |
| 3210691A1 | 9/1983 | Fed. Rep. of Germany . | |
| 3501339 | 7/1986 | Fed. Rep. of Germany | 128/643 |
| 2172979 | 1/1973 | France . | |
| 2569976 | 3/1986 | France . | |
| 2575917 | 6/1986 | France . | |
| 392847 | 5/1933 | United Kingdom . | |
| 1340756 | 12/1973 | United Kingdom . | |
| 1367254 | 9/1974 | United Kingdom . | |
| 1451537 | 10/1976 | United Kingdom . | |
| 2057046B | 1/1983 | United Kingdom . | |
| 2148719B | 1/1987 | United Kingdom . | |
| WO85/00018 | 1/1985 | World Int. Prop. O. . | |

OTHER PUBLICATIONS

European Search Report Based on No. 9008764.
An English Language Abstract and Claim 1 Translation of DE 32 10 691.
An English Language Abstract and Claim 1 Translation of DE 28 30 412.
An English Language Abstract and Claim 1 Translation of DE 27 49 048.
An English Language Abstract and Claim 1 Translation of DE 27 42 058.
An English Language Abstract and Claim 1 Translation of FR 2,575,917.
An English Language Abstract and Claim 1 Translation of FR 2,569,976.

Primary Examiner—Lee S. Cohen
Attorney, Agent, or Firm—Beveridge, DeGrandi, Weilacher & Young

[57] ABSTRACT

A non-invasive medical probe for monitoring a patient's condition in particular an intra-uterine device for monitoring fetal condition is featured. The medical probe includes a resilient walled suction cup having a peripheral rim for application to a patent's skin, a pump adapted for connection to the cup for evacuating the cup to adhere the cup to the patient's skin, and a pair of non-invasive skin contact electrodes for connection to diagnostic apparatus. One of the electrodes is disposed on a mounting located centrally within the cup to leave a channel to be evacuated by the pump and the second electrode is disposed externally of the cup adjacent to the cup to provide a second contact in the vicinity of the first electrode.

21 Claims, 6 Drawing Sheets

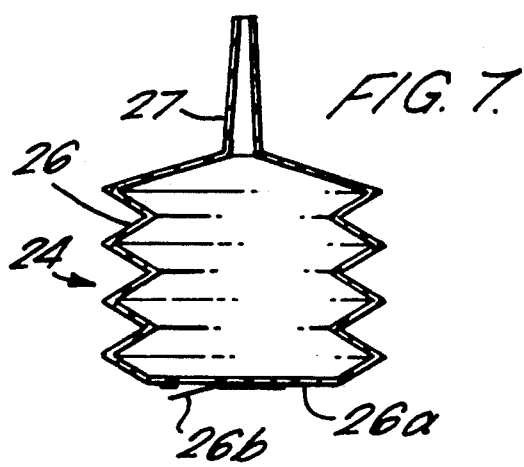
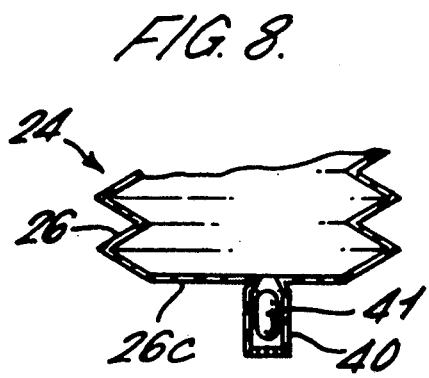
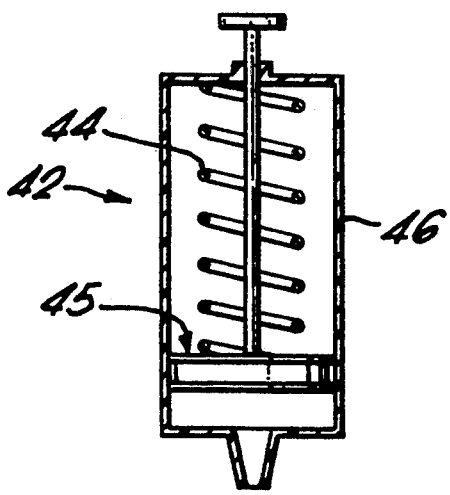
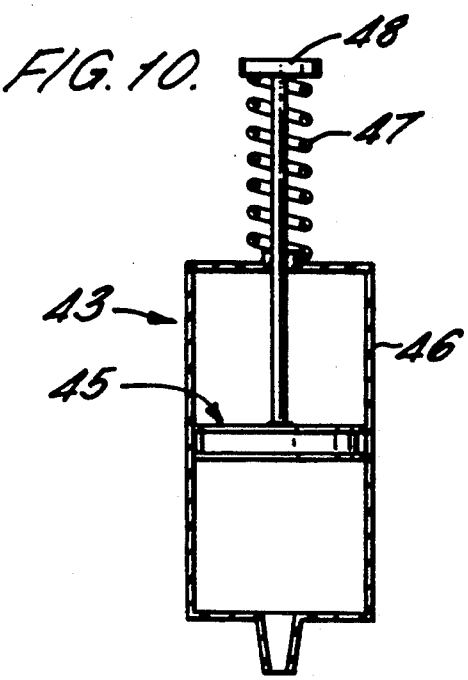
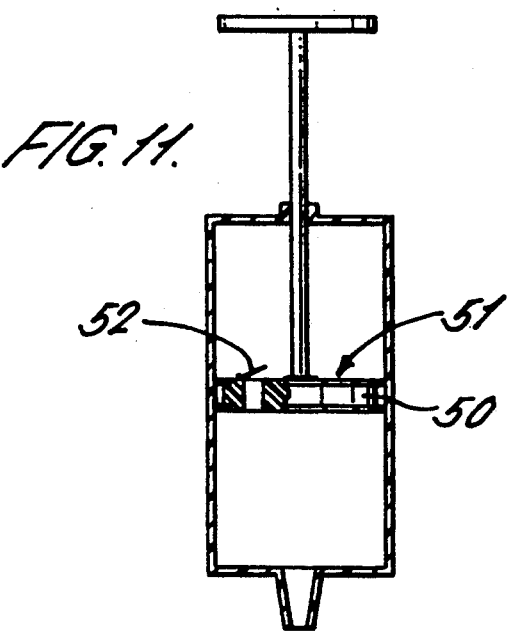

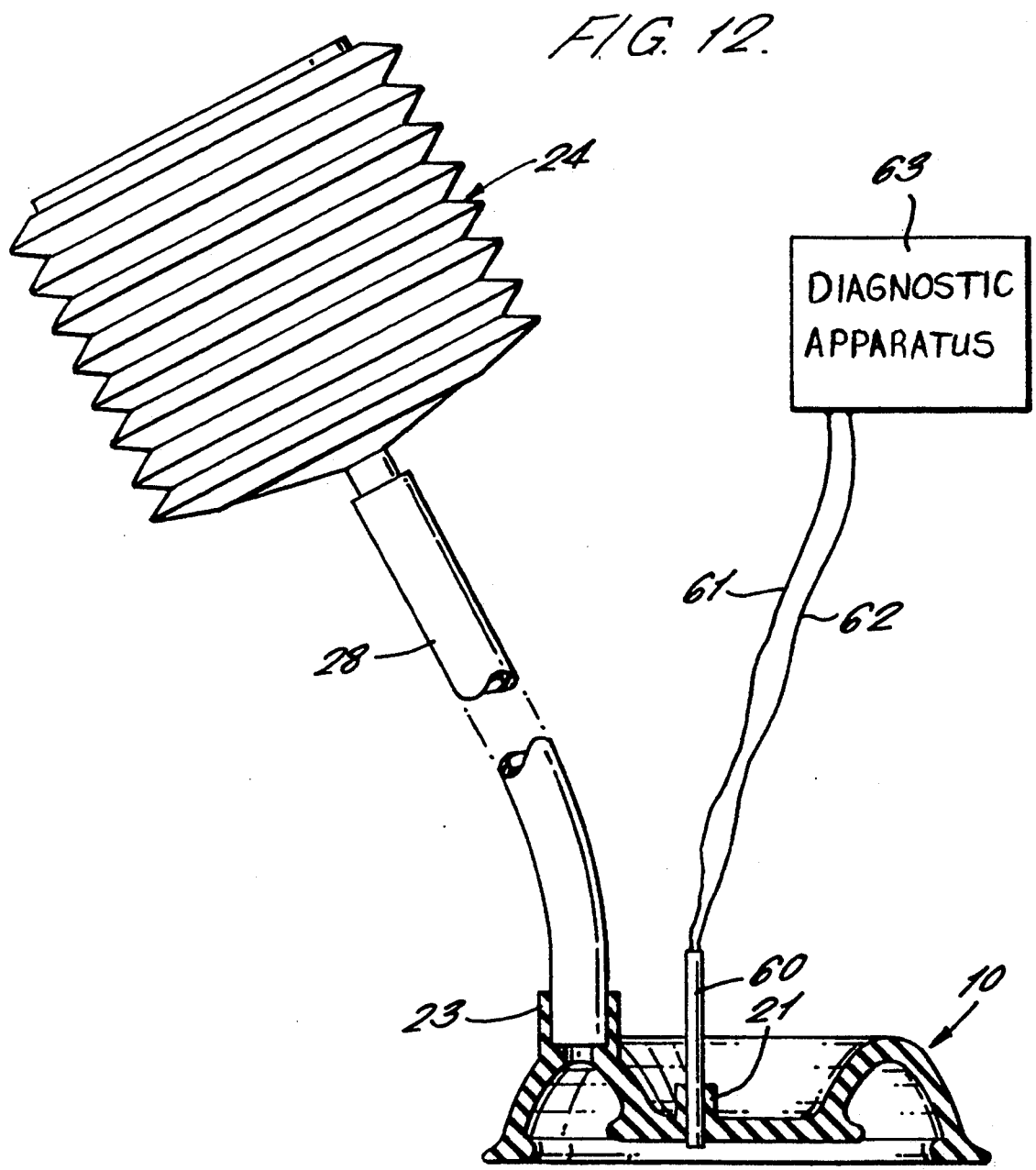

NON-INVASIVE MEDICAL PROBE PROVIDED WITH SUCTION CUP

FIELD OF THE INVENTION

This invention relates to non-invasive medical probes for monitoring a patient's condition and to suction cups therefor.

BACKGROUND DISCUSSION

It is commonly required in medical fields to secure a probe including an electrode adjacent the surface of a patient's skin for measuring and monitoring purposes. It is also desirable to secure an electrode adjacent the scalp of a fetus or a neonate without such securing causing trauma to the patient, as is conventionally caused by invasion of the fetus or neonate.

FR-A-2569976 discloses a resilient suction member for securing an electrode adjacent the surface of a patient's skin, in which a resilient boss has secured therein a plurality of concentrically mounted electrodes one of which, namely a monitoring pick-up, is exposed on the face of the boss which is applied to the skin. The exposed electrode is surrounded by three concentric, shallow channels formed in the otherwise flat face of the boss. The channels are connected via passageways to a source of sub-atmospheric pressure in the form of a vacuum pump so that, when the face of the boss is applied to the skin, the chamber formed by the channels and the skin may be evacuated with the result that the boss, and hence the electrode, is secured by suction against the skin.

The suction member of FR-A-2569976 suffers the disadvantage that the channels are necessarily small dimensions when the suction member itself is manufactured small enough for application to the scalp of a neonate or a prenatal fetus. Consequently the area of scalp over which the reduced pressure in the channels acts, and hence the downward securing force, is small. This downward force is spread over a multiplicity of upwardly directed supporting rings with the result that the sealing effect of the suction member is small. To overcome the prospect of resulting leakage, the source of sub-atmospheric pressure required to retain the monitoring pick-up in secure contact with the monitored surface, has to be one which can pump out the cavity indefinitely, i.e. a mechanical/electrical pump. Such pumps are costly and bulky. This arrangement may be uncomfortable for the patient, and it is in addition frequently required to supplement the securing action of the suction member with surgical adhesive tape as the suction created in a small suction member is barely sufficient to retain the electrode adjacent the scalp. For these reasons it is believed that this proposed suction member has not achieved practical use, especially in connection with the monitoring of a pre-natal fetus or as an intra-uterine device.

U.S. Pat. No. 4,217,908 and U.S. Pat. No. 4,369,793 disclose medical instrumentation electrode apparatus for use in connecting wiring from an external medical instrument such as an electrocardiograph machine with an area of a patient's skin. The apparatus includes a vacuum bell which is interconnectible with a resilient bulb for partially evacuating the same and causing a pliable ring disposed on the open end of the bell to collapse against a patient's skin. In this manner a disposable contact held in place within the vacuum bell by a core portion of the bell is held in electrical contact with the skin area. The core portion is integrally formed with the vacuum bell and includes an upper protruding end for connection with the resilient bulb and is further provided with an air communicating passage extending between the bulb and the interior of the vacuum bell. A single electric contact is provided for connecting a wire from an electrocardiograph machine to the contact.

WO-A-85/00018 discloses an electrode unit for use in electrotherapy comprising a cup that is collapsible by suction applied to a pipe that forms the stem of an electrode disc within the cup. Conduits communicate the inside of the cup through a boss with the atmosphere through an external groove. A sleeve extends from the boss and has a circumferential rib or flange. The sleeve can be folded back to engage the flange into the groove to block off the conduits which connect to atmosphere to permit the cup to collapse when the rim of the cup is placed against the body of a patient and suction is applied, and the sleeve can be lifted up to admit air into the conduits in order to release the cup.

It will be appreciated that none of the arrangements described in the aforesaid US and International references would be suitable for application to the head of an unborn fetus located in the mother's uterus for monitoring the condition of the fetus.

SUMMARY OF THE INVENTION

This invention provides a non-invasive medical probe for monitoring a patient's condition comprising a resilient walled suction cup having a peripheral rim for application to a patients skin, the cup being adapted for connection to a source of suction for evacuating the cup to secure the cup to the patient's skin, and a pair of non-invasive skin contact electrodes for connection to diagnostic apparatus, one of the electrodes being disposed internally within the cup on a mounting located centrally within the cup to leave a channel encircling the electrode within the peripheral rim to be evacuated for securing the cup to the skin, and the second electrode being disposed on an external surface of the probe adjacent to the cup to provide a second contact in the vicinity of the first electrode, the first electrode and its mounting being disposed in a plane located behind the peripheral rim of the cup when the cup is in the relaxed condition so that initial contact with the patient's skin is made at the peripheral rim of the cup and, following evacuation of the channel in the cup, the internal electrode makes contact with the patient's skin to obtain a signal at the skin surface responsive to a varying condition of the patient, characterised in that the source of suction comprises an individual suction pump adapted for connection to the cup, and the resilience and form of the cup are such that, when in contact with a patient's skin and subjected to suction, the wall of the cup deforms allowing the internal electrode to be drawn down onto the patient's skin to make the required contact therewith.

An advantage of this arrangement over the suction member of FR-A-2569976 is that, for a particular size of suction cup, the suction in the chamber formed between the channel and the patient's skin surface acts over a larger area than in prior devices, so the force retaining the suction cup against the surface is correspondingly greater. To this increased retaining force is further added the further retaining force which originates from drawing forwardly the central electrode mounting portion within the suction cup, and this further retaining force is transmitted to the rim of the partial stiffness of the cup material. Furthermore, this increased force is concentrated on a single rim rather than being distributed over a multiplicity of upwardly directed supporting rings as in the suction member of FR-A-2569976. These two features—the increased retaining force and the concentrating of its action—create a greatly improved seal around the suction cup, and in turn permit the use of relatively simple, low pressure source means, such as a manually operated bellows, with the advantages of lightness, compactness and low cost, and also with lower suction level than that which would be harmful.

Furthermore, the location of the external electrode is such that when the suction cup is used at an internal location such as within the uterus or womb, the two electrodes pick up signals from closely spaced points; this is the case of fetal scalp monitoring because it focuses on the fetal signal rather than possibly the mother's signal.

The invention also provides a suction cup formed of resilient material to be secured by suction to a patient's skin, comprising a peripheral wall, a centre portion enclosed by the peripheral wall to define a channel therebetween, and means for connecting the channel of the cup to a source of suction, the lower face of the centre portion being disposed in a plane behind the edge of the peripheral wall, wherein the peripheral wall and the centre portion each have a respective lip projecting inwardly of the channel to provide the channel with an undercut configuration in cross-section into which the skin is drawn by the suction created within the channel, the oppositely directed lips acting to entrap the drawn in skin surface thereby enhancing the security of attachment of the suction cup.

BRIEF DESCRIPTION OF THE DRAWINGS

There now follows a description of some specific embodiments of the invention, by way of example, with reference being made to the accompanying drawings, in which:

FIGS. 7 to 11 show further forms of bellows and other suitable pumps; and

FIG. 12 is a schematic elevational view, partly in section, which is similar to FIG. 6, but is directed to the suction cup of FIG. 2 and includes a monitoring device of any suitable form connected to diagnostic apparatus.

DETAILED DESCRIPTION OF THE PREFERRED EMBODIMENTS

Figure 1:
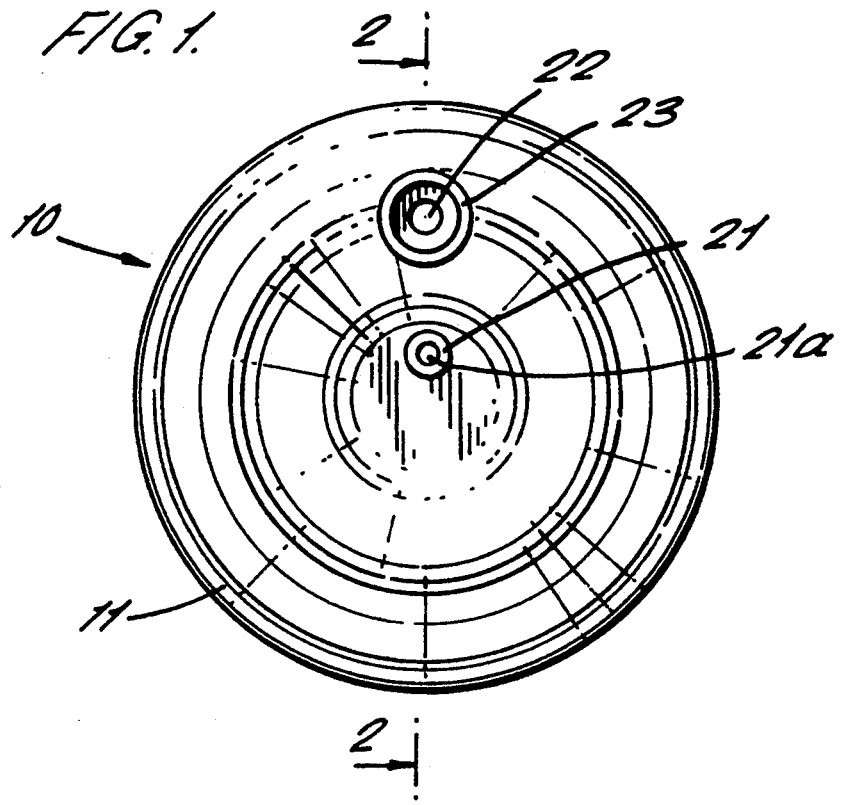
FIG. 1 is a plan view of a first embodiment of a resilient suction cup as part of a non-invasive medical probe according to the invention.
Figure 2:
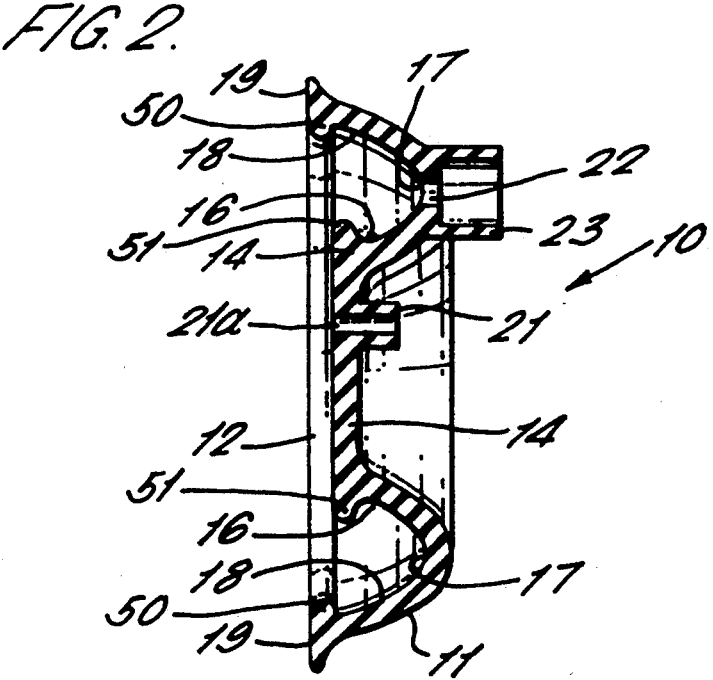
FIG. 2 is a vertically sectioned view taken along line 2—2 of FIG. 1.

Referring to FIGS. 1 and 2 of the drawings, there is shown a suction cup 10 which is generally circular in plan and formed of resilient material.

Suction cup 10 has a peripheral wall 11 which is substantially continuous on the upper face of the suction member as shown, the suction cup 10 having an opening 12 in its lower face.

Peripheral wall 11 defines within opening 12 a centre portion 14 which is generally circular, and the outer periphery of which is integral with the inner wall 16 of a single annular channel 17 formed about centre portion 14. In this embodiment, channel 17 is an annular channel, and portion 14 and channel 17 are generally concentric with the circular plan of the suction cup 10.

Channel 17 defines a recess relative to portion 14 and its shape in cross-section, as seen in FIG. 2, is arched towards its upper inner aspect such that it will withstand substantial negative pressure without collapsing during its intended use. This allows the suction cup to be formed from material which is pliable enough to form a good seal over an irregular surface. Outer wall 18 of channel 17, opposite inner wall 16, is formed by part of the peripheral wall 11 and terminates in an annular rim 19 which forms the outermost periphery of the suction cup 10.

The inner aspect of the annular rim 19 and the outer aspect of the centre portion 14 at its outwardly directed face are shaped to provide lips 50, 51 respectively projecting inwardly of the channel 17 to give the channel 17 an undercut configuration in vertical cross-section which allows the channel, during use of the suction cup 10, to entrap the drawn in skin surface thereby enhancing the security of attachment of the suction cup to the fetal head.

The upper surface of centre portion 14 as shown includes an upstanding sleeve 21 which is formed integrally with centre portion 14. Sleeve 21 has a central bore 21a which extends through the centre portion 14 for reception of an electrode support attached to an electrode contact plate beneath the lower surface of the centre portion as described below in connection with the embodiment of FIG. 3.

A passageway 22 communicates the interior of channel 17 with the exterior of the suction cup 10. Passageway 22 opens into sleeve 23 which is upstanding on the uppermost, annular ridge of channel 17 on the exterior of suction cup 10. Sleeve 23 surrounds the end of passageway 22.

Figure 3:
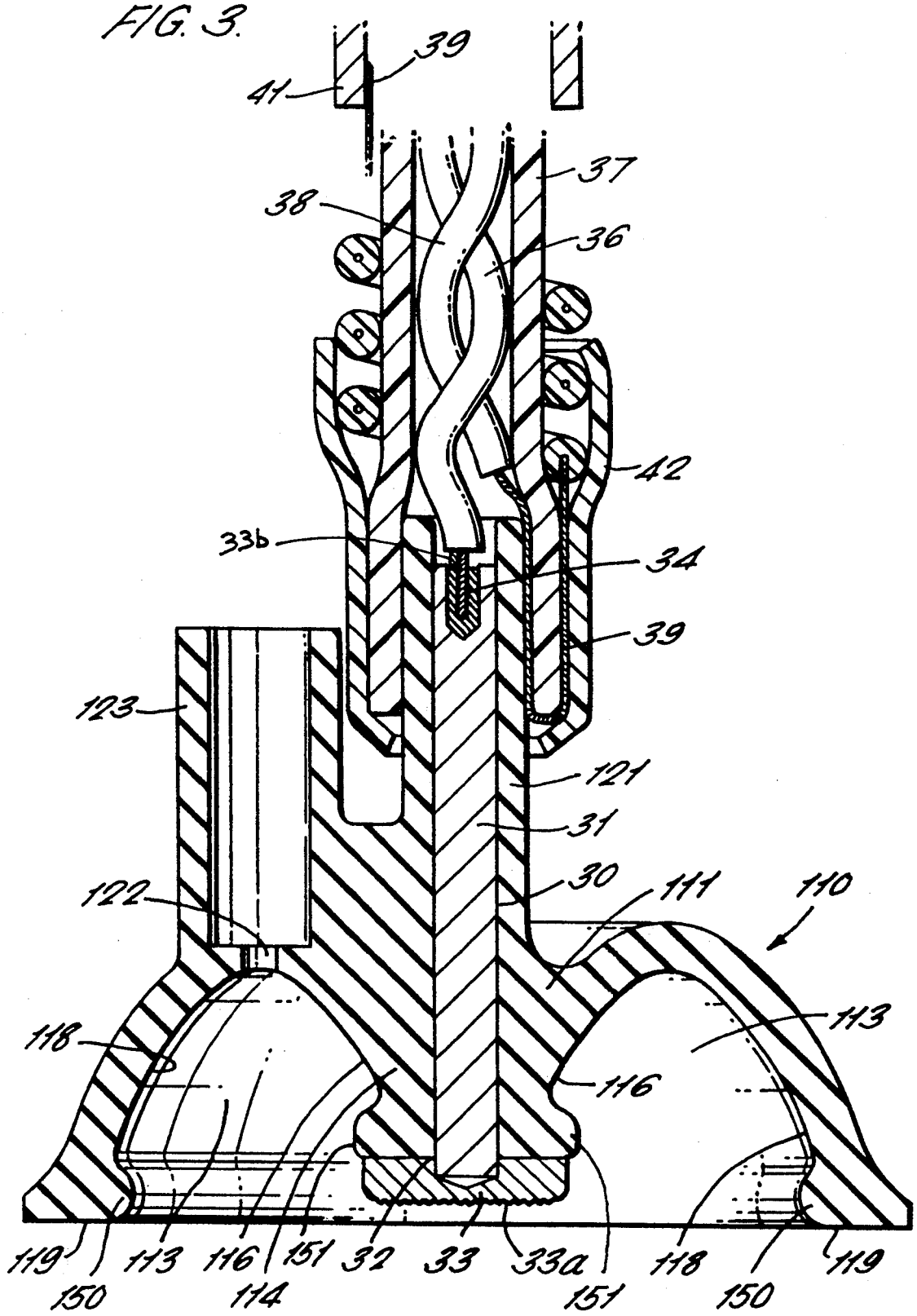
FIG. 3 is a vertically sectioned view of a second embodiment of a resilient suction cup including a pair of electrodes.

Referring to FIG. 3, there is shown a second embodiment of a resilient suction member 110.

In the embodiment of FIG. 3 the shape and function of the centre portion 114, inner wall 116, outer wall 118, channel 113 formed between walls 116 and 118, rim 119, lips 150, 151, passageway 122 and sleeve 123 are substantially the same as those of their counterpart centre portion 14, walls 16, 18, channel 17, rim 19, lips 50, 51, passageway 22 and sleeve 23 in the embodiment of FIGS. 1 and 2.

Centre portion 114 is of reduced diameter in the embodiment of FIG. 3 as compared with centre portion 14 of FIGS. 1 and 2 although channel 113 is of the same width as channel 17, so the diameter of suction cup 110 is less than that of suction cup 10 of FIG. 1.

The generally arched shape of the channel 113, in vertical cross-section, likewise corresponds to the channel 17 of FIGS. 1 and 2 whereby the channel will not collapse with the required negative pressure applied during use. The inwardly lipped undercut configuration of the channel 113 will also entrap the drawn in skin surface to achieve the required security of attachment of the suction cup to the fetal head.

Passageway 122 is formed in approximately the same region of channel 113 as is passageway 22 in channel 17 in the embodiment of FIGS. 1 and 2.

In the region backing centre portion 114 the wall 111 of suction cup 110 is thickened into a boss having a cylindrical bore 30 which is concentric with the suction cup 110. Bore 30 opens into sleeve 121 which is upstanding centrally in the upper surface of suction member 110.

In the embodiment of FIG. 3, sleeve 121 and bore 30 have received therein an elongate, axially extending, electrically conductive electrode support 31 which terminates at its lower end in a shallow cone which protrudes through an aperture 32 formed in centre portion 114 and has an electrode contact plate 33 secured on the conical end. The centre portion 114, thereby provides a mounting for the electrode support 31 and electrode contact plate 33 which is disposed internally of the suction cup 110. Electrode contact plate 33 is of a kind suitable for the measuring and/or monitoring to be undertaken through application of the suction cup 110. The electrode contact plate 33 may optionally be formed of or coated with a substance improving the conduction of signals from the patient to the electrode. The plate may be formed from metal and may have a roughened or knurled surface to enhance contact with the skin particularly in the case of a hair covered scalp as indicated at 33a.

At its upper end, electrode support 31 includes a bore 34 which receives a live electrode wire 36 which is in electrical contact with the electrode support and hence the electrode contact plate 33.

Electrode wire 36 is housed within a silicone rubber sheath 37 which is fitted over the end of sleeve 121 by virtue of the resilience of its material.

Twisted about live electrode wire 36 within sheath 37 is a neutral electrode wire 38. The conductor 39 of neutral wire 38 is bared over a part of its length to permit the conductor 39 to pass between sheath 37 and sleeve 121. Conductor 39 then passes up the outside of sheath 37 to a region in which the insulation of neutral wire 38 is re-formed on conductor 39 and in which neutral wire 38 is coiled about the exterior of sheath 37.

Neutral wire 38 is coiled several times about sheath 37 in the embodiment of FIG. 3 and at its upper end the conductor 39 is electrically connected to a sliding electrical contact or second electrode 41 comprising a metallic sleeve external of the suction cup 10.

A resilient, insulating outer sleeve 42 is fitted about the exterior of sheath 37 to protect the exposed conductor 39 and the lowermost coils of coiled wire 38 against accidental damage.

Figure 4:
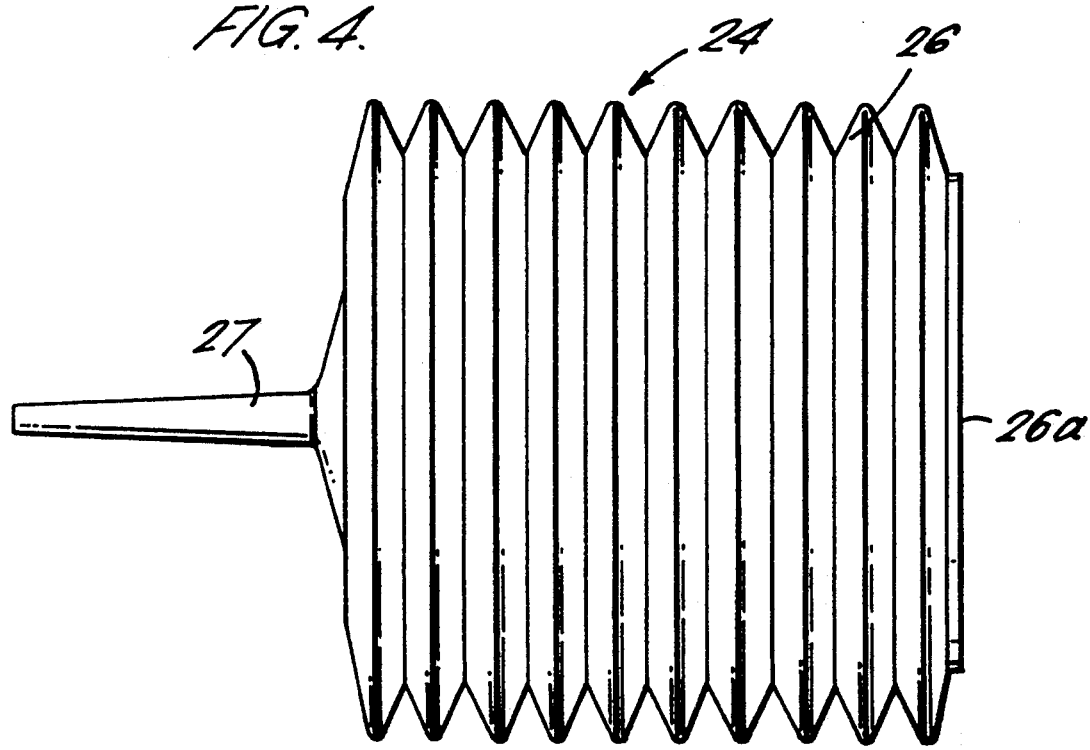
FIG. 4 is a side elevational view of a bellows suitable for use as pump means for the suction cups of FIGS. 1 to 3.
Figure 5:
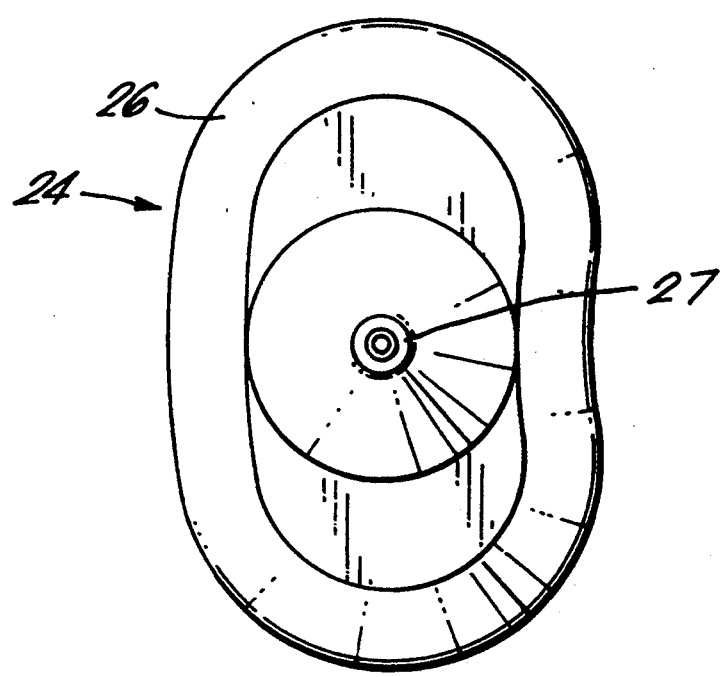
FIG. 5 is an end elevational view of the bellows of FIG. 4.
Figure 6:
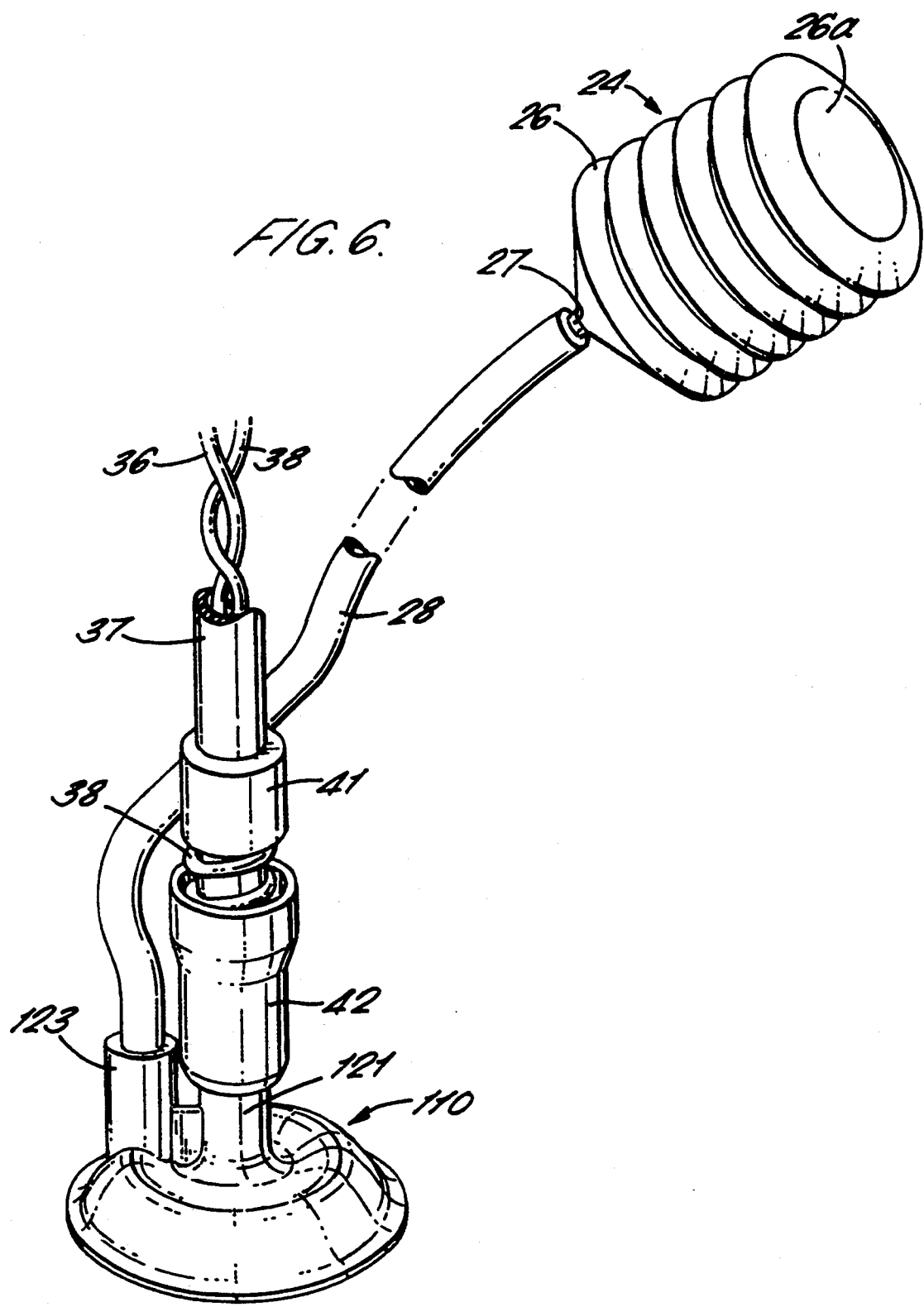
FIG. 6 is a perspective view of the suction cup of FIG. 3 and a bellows similar to the bellows of FIG. 4 connected together.

In FIGS. 4 to 5 there is shown a simple, manually operated bellows 24 for use with the suction cup 10 or 110 to complete the non-invasive probe. The bellows 24 may be of generally oval cross-section as shown in FIG. 5 or may be circular in cross-section as shown in FIG. 6, and includes a resiliently compressible, variable volume pumping chamber 26 which is closed at one end by an integral end wall 26a and has an integral nozzle 27 communicating with the exterior of the chamber at the opposite end. The resilient walls of the pumping chamber 26 tend to bias the bellows 24 towards its expanded condition. Preferably the bellows 24 is connected by a flexible tube or conduit connection 28 to the suction cup 110 as illustrated in FIG. 6 to enable the bellows to be located remotely from the cup. This arrangement is particularly necessary in the case where the suction cup is applied to the head of an unborn fetus still within the mother's uterus so that the bellows can be located and operated externally of the mother.

Compressing of the pumping chamber 26 of the bellows 24 in an axial direction causes expulsion of air from chamber 26 via nozzle 27. Releasing of the pumping chamber causes the pumping chamber 26 to tend to resume its uncompressed configuration, with the resulting simultaneous increase in its volume causing the bellows to be operable as a simple suction pump. More complex suction pumps, for example including selectively operable non-return valve means, may be used with the suction members of the invention instead of the bellows of FIGS. 4 and 5, but the bellows 24 has been found to be sufficiently powerful to operate the suction member 10 and is, in addition, light, reliable, easily sterilised and cheap to manufacture.

The operation of the resilient suction cup of the invention will now be described in relation to the embodiment of FIGS. 1 and 2, although it should be realised that the operation of the embodiment of FIG. 3 takes place in a similar manner.

Prior to application of the suction cup 10 to the skin of a patient, an electrode assembly such as 31, 33, 36, 38 of FIG. 3 is inserted into the bore of the sleeve 21 in the centre portion 14, the electrode contact plate 33 being beneath the lower surface of the centre portion 14. The dimensions of the bore of sleeve 21 are so chosen that the electrode support 31 is frictionally retained within the bore, with said pliability of the material of the suction cup allowing the electrode contact plate 33 o to assume appropriate orientation to permit it to receive electrical signals from the patient.

The electrode is suitable for monitoring characteristics of a patient such as a fetus or a neonate, and it may be connected via suitable wiring to diagnostic monitoring apparatus.

The nozzle 27 of the bellows 24 is connected in this embodiment by pipe 28 to the sleeve 23 surrounding the end of passageway 22. The pipe 28 is a sealing fit in sleeve 23, so that the bellows may be operated to withdraw air from channel 17 via passageway 22.

With the suction cup 10 thus arranged, the pumping chamber 26 is axially compressed to expel air therefrom, via passageway 22 and opening 12. In that condition the suction cup 10 is applied to, for example, the scalp of a fetus with the rim 19 of the suction member 10 in sealing contact with the surface of the scalp. The air line 28 and cable 36, 38 extend out through the vagina, and the second electrode 41 on the cable bears against and is in electrical contact with the mother at a location not far away from the first internal electrode, i.e. the position of the electrode contact plate 33. The cable is connected to an electrocardiogram machine or other diagnostic apparatus, and the bellows is accessible outside the mother.

Within the suction cup 10, a chamber then exists between the inner side of peripheral wall 11 and the surface of the scalp, the chamber being sealed about rim 19 of wall 11. Releasing of the pumping chamber 26 causes it resiliently to tend to return to its uncompressed configuration, withdrawing air from the chamber in the suction cup and adhering the member 10 by suction to the surface of the scalp.

As a result of the shape of suction cup 10, the partial vacuum in the chamber resulting from operation of the bellows as aforesaid acts initially over the entire area of the surface of the scalp enclosed within rim 19.

However, the suction cup 10 tends to deform as the partial vacuum is applied, with the result that central portion 14 is drawn downwardly, against the resilience of the suction cup material, whereby the electrode contact plate 33 engages the surface of the scalp. The electrode contact plate 33 is thereby ideally positioned for monitoring purposes in contact with the scalp, the circuit being completed through the second electrode 41 which is in contact with the mother at a point close to the suction cup 10 and which, of course, is in contact with the fetal head. In practice, it is found that the close proximity between the second electrode 41 and the area of application of the internal electrode within the suction cup 10 is important to ensure that the desired signal transmitted by the probe to the electrocardiogram machine or other diagnostic apparatus is representative of the fetus being measured or monitored and not of the mother.

As the electrode plate 33 contacts the scalp surface, the shape of the single chamber formed between the suction cup and the scalp surface becomes substantially annular, conforming to the channel 17, and the force pulling the plate 33 towards the scalp surface (calculated as the area of the plate multiplied by the lowering of the pressure, as prevailing in the channel, below atmospheric) is transmitted via walls 16 and 18 to rim 19. The excess of the atmospheric pressure over the pressure prevailing inside the channel acts on the large, annular area of the scalp surface enclosed between the rim 19 and the electrode contact plate 33 and approximately half of the resulting force acts vertically downwards through the rim 19 to retain the suction cup 10 strongly secured to the scalp surface and to prevent air or ambient liquids seeping into the suction cup. Since the retaining force acts on a single rim 19 the overall security of holding the suction cup in position on the fetal head and hence the sealing of the cup against the skin surface is greater than in arrangements where the retaining force acts via a plurality of rims or walls.

During the application of suction, the annular channel 17 entraps the drawn in skin surface of the scalp which conforms to the arched cross-sectional shape of the channel, the undercut configuration described above enhancing the security of the suction cup 10 to the fetal head. The moderate sub-atmospheric pressure applied by the bellows 24 is maintained to act against perturbations tending to dislodge the cup.

After the monitoring process is completed, release of the suction cup 10 is readily achieved by axially re-compressing the pumping chamber 26 to blow air via nozzle 27 through passageway 22 to increase the pressure in the channel 17 and to permit withdrawal of the suction cup from the scalp surface rather than just ripping the cup off.

Reference is now made to FIGS. 7 to 11 of the drawings which show a number of modifications to the arrangements described above. Firstly, in FIG. 7, a modification to the bellows 26 is illustrated in which the closed end wall 26a of the bellows is formed with a flap valve 26b which can open to release air from the bellows through a port in the end wall 26a as the bellows is compressed. Thus, if it is necessary to re-establish the suction holding the suction cup to the head of the fetus whilst the probe is in use, the bellows 26, which as described above is outside the mother, can be recompressed allowing air from the bellows to escape through the flap valve 26b and not be transmitted to the suction cup, and the user's thumb acting on the end wall of the bellows can then be moved over the flap valve to close the valve port as the bellows is allowed to expand to re-draw the vacuum in the suction cup.

FIG. 8 shows a different form of non-return valve on the end wall 26c of the bellows in which a short tube 40 projects from the end wall of the bellows and has a ball or slug 241 held captive in the tube to allow release of air through the tube when the bellows is compressed. In this embodiment, in the outer end of the tube is a grid to retain the slug 241 therein without closing off the end. When the bellows is allowed to expand, the slug 241 is drawn against the valve seat to block the opening between the tube 40 and bellows 26 so that the bellows then draws vacuum in the suction cup. For releasing the suction cup without damaging the skin of the fetus, the valve is held closed when the bellows is compressed.

The resilient walled bellows 26 described above provides a convenient form of hand operated pump for drawing vacuum in the suction cup, but it will be appreciated that other forms of pump means can be utilised and FIGS. 9 and 10 show syringes 242, 43 respectively adapted to act as pumps for evacuating the suction cup. In FIG. 9 the pump has an internal tension spring 44 so that when the plunger 45 of the pump has been depressed and the suction cup is applied to the patient's skin, the plunger can be released and, under the action of the spring, the plunger draws vacuum in the suction cup as it is moved along the cylinder 46 of the syringe. FIG. 10 shows a similar arrangement in which the spring 47 is a compression spring located externally between the head 48 of the plunger 45 and the end of the cylinder 46 of the syringe which is opposite to the nozzle end. FIG. 11 shows a modified form of syringe in which the piston 250 of the plunger 251 has a non-return valve 252 so that as the plunger is depressed, air is released to the back of the piston and is not directed towards the suction cup. When the plunger 251 is released and allowed to return, for example, by a spring 44 or 47, the non-return valve 252 closes automatically so that the return movement of the plunger draws vacuum in the suction cup as described above.

The above embodiments relate to a probe for non-invasively monitoring, generally the heart beat of a fetus, by the use of suction to secure the suction cup 10 or 110 to the fetal head, and the pair of electrodes 33, 41 connected to diagnostic apparatus.

Additionally or alternatively, it may be desired to monitor other conditions of the patient.

With reference to FIG. 12, there is illustrated an embodiment in which the suction cup 10 of FIGS. 1 and 2 has a monitoring and/or measuring device 60 connected by wires 61, 62 to the schematically illustrated diagnostic apparatus 63, the device 60 passing through bore 21a in the sleeve 21 upstanding from the central portion 14 of the cup and making skin contact with the patient. Bellows 24 is also connected by pipe 28 to sleeve 23. Application of the suction cup is the same as described previously.

However, it will be appreciated that the monitoring and/or measuring device may be provided as an additional device or instead of the electrode monitoring device of the preceding embodiments.

More particularly, at least one additional device may be employed for obtaining other biological information signals, from which signals information is deduced concerning fetal condition, by application of the device to the skin surface.

One example is the use of fibre optics for the emission and reception of light at the skin surface, such as for monitoring skin blood perfusion. The fibre optics connected to the diagnostic apparatus would pass through the sheath 37, which would be enlarged if necessary, and the sleeve 21 or 121 in the centre portion of the respective suction cup, and also through apertures in the electrode contact plate 33, if retained, into contact with the skin surface.

A transducer may be employed for the conversion of biological information into an electric signal, the information being, for example, the amounts of oxygen and/or carbon dioxide in the blood. Again the transducer would be connected back by wires through the centre portion of the suction cup to the diagnostic apparatus.

A thermistor or other similar device may measure skin surface temperature. The thermistor mounted on the bottom face of centre portion 14 or 14, would contact the fetal skin, through an aperture in the electrode contact plate 33 if retained, and have a pair of wires passing back through the centre portion 14 or 114, and if desired the sheath 37, to the diagnostic apparatus.

Another example is the use of piezo crystals for the generation and receiving of ultrasound signals. The crystals would be mounted on the bottom face of centre portion 14 or 114, with apertures in the electrode contact plate 33 if retained, wires from the crystals again passing back through the centre portion of the suction cup to the diagnostic apparatus.

A further example is the use of at least two oximetry devices mounted in the same manner as the above-mentioned piezo crystals and connected by wires to the diagnostic apparatus. The oximetry devices would measure haemoglobin oxygen saturation.

It will again be appreciated that all these additional devices would pass through the central portion 14 or 114 of the suction cup to make contact with the skin surface. With regard to the construction of the suction cup shown in FIG. 3, the devices would contact the skin through the electrode contact plate 33. However, in the case of an enlarged centre portion being provided, for example as shown in FIG. 2, this may not be necessary.

The above examples are, of course, not exhaustive, and other similar uses are envisaged within the scope of the invention.

What we claimed is:

1. A non-invasive medical probe for monitoring a patient's condition comprising:
   a suction cup having a resilient wall with peripheral rim for application to a patient's skin;
   a source of suction which comprises an individual suction pump connected to said cup;
   a first and a second non-invasive skin contact electrode adapted for connection to a diagnostic apparatus, the first electrode being disposed internally within the cup on a mounting located centrally within the cup to leave a channel encircling the first electrode within the peripheral rim to be evacuated for securing the cup to the skin, and the second electrode being disposed on an external surface of the probe adjacent to the cup whereby the second electrode provides a second contact in the vicinity of a contact of the first electrode, the first electrode and said mounting being disposed in a plane located behind the peripheral rim of the cup when the cup is in a relaxed or non-suction condition so that initial contact with the patient's skin is made at the peripheral rim of the cup and, following evacuation of the channel in the cup by said suction pump, the first electrode makes contact with the patient's skin to obtain a signal at the skin surface responsive to a varying condition of the patient, and the cup having a resilience and form such that, when the cup is in contact with a patient's skin and subjected to suction, the wall of the cup deforms allowing the first electrode to be drawn down onto the patient's skin to make contact therewith.

2. A non-invasive medical probe as claimed in claim 1, wherein the mounting for locating the first electrode comprises a centre portion which is integral with the peripheral rim of the cup and which is disposed within the cup to define an inner wall of the channel surrounding the first electrode mounted on the centre portion.

3. A non-invasive medical probe as claimed in claim 1, wherein a cable is connected to the suction cup comprising electric wires for connection to the respective electrodes, and said first electrode being connected to one of said wires and said second electrode comprising a metallic sleeve encircling the cable adjacent to the suction cup and to which a second one of said wires is electrically connected.

4. A non-invasive medical probe as claimed in claim 1 wherein the pump for drawing vacuum within the channel in the cup includes a variable volume chamber connected to the channel in the cup and resilient means for urging the chamber into an expanded condition to maintain a partial vacuum drawn by the pump in the channel in the cup.

5. A non-invasive medical probe as claimed in claim 4, wherein said pump includes an air pressure release valve which is in communication with said chamber for discharging air from the chamber without applying pressure to the air within the channel of the cup.

6. A non-invasive medical probe as claimed in claim 5, wherein the release valve for the chamber comprises a releasable one-way valve.

7. A non-invasive medical probe as claimed in claim 1, wherein the pump comprises a bellows providing a chamber which is collapsible to discharge air therefrom against the action of resilient means to expand the bellows to draw vacuum in the channel connected thereto.

8. A non-invasive medical probe as claimed in claim 7, wherein the bellows has resilient walls formed to bias the bellows towards its expanded condition.

9. A non-invasive medical probe as claimed in claim 8 wherein the bellows includes a resilient flap valve for release of air therefrom when the bellows is compressed and to prevent entry of air thereto when the bellows is released.

10. A non-invasive medical probe as claimed in claim 9, wherein the bellows is a generally closed cylindrical form, one end wall of which has a conduit connection to the channel in the suction cup and the opposite end wall of which is formed with a port controlled by said flap valve.

11. A non-invasive medical probe as claimed in claim 1, wherein the pump comprises a cylinder and a reciprocable piston for varying the volume of a chamber provided in the cylinder, spring means being provided for biassing the piston in a direction to expand the chamber and thereby draw vacuum in the resilient suction cup connected to the chamber.

12. A non-invasive medical probe as claimed in claim 11, wherein the piston has a plunger projecting outwardly of the cylinder for manual operation of the piston.

13. A non-invasive medical probe as claimed in claim 12, wherein the piston includes a one-way valve to release air from the variable volume chamber of the cylinder connected to the channel of the suction cup prior to application of the suction cup to the patient's skin, and then to draw vacuum in the channel to hold the cup on the patient's skin by the action of the spring means on the piston in trying to restore the chamber of the cylinder connected to the suction cup to its expanded position.

14. A non-invasive medical probe as claimed in claim 1 wherein said suction cup includes means for connecting the channel of the cup to said source of suction, and the peripheral rim and the mounting located centrally within the cup each have a respective lip projecting inwardly of the channel to provide the channel with an undercut configuration in cross-section into which the skin is drawn by the suction created within the channel, the oppositely directed lips acting to entrap the drawn in skin surface thereby enhancing the security of attachment of the suction cup.

15. A non-invasive medical probe as claimed in claim 14, wherein the channel is defined by an arched portion of the wall of said suction cup which arched portion is shaped so as to resist collapse when subjected to suction.

16. A non-invasive medical probe as claimed in claim 14, further comprising a monitoring and/or measuring device which is in addition to said first electrode and is supported in said mounting for making contact with the patient's skin to obtain a biological information signal at the skin surface responsive to one or more conditions of the patient.

17. A non-invasive medical probe as claimed in claim 14, wherein the means for connecting the channel to a source of vacuum pressure is a sleeve directed outwardly from the wall of the suction cup and said sleeve having a passageway which extends through the wall of the suction cup into communication with said channel.

18. A non-invasive medical probe as claimed in claim 14, wherein the connecting means includes a flexible conduit which is dimensioned and arranged to allow the suction cup to be secured to a fetal scalp by way of the source of suction located externally of the patient.

19. A non-invasive medical probe as claimed in claim 1, further including a monitoring and/or measuring device which is in addition to said first and second electrodes and is supported in the mounting of the cup, and said monitoring and/or measuring device being adapted for connection with a diagnostic apparatus.

20. A non-invasive medical probe as claimed in claim 1, wherein said first electrode includes an electrode contact plate with a roughened surface.

21. A non-invasive medical probe for monitoring a patient's condition, comprising:
a resilient walled suction cup having a peripheral rim for application to a patient's skin;
a suction pump connected to said cup;
a first and a second non-invasive skin contact electrode adapted for connection to a diagnostic apparatus, the first electrode having an electrode supply being slidingly received within a bore formed in said suction cup and an electrode contact plate disposed internally within the cup on a mounting located centrally within the cup to leave a channel encircling the first electrode within the peripheral rim to be evacuated for securing the cup to the skin, and the second electrode being disposed on an external surface of the probe adjacent to the cup whereby the second electrode provides a second contact in the vicinity of a contact of the first electrode, the electrode contact plate of said first electrode and said mounting being disposed in a plane located behind the peripheral rim of the cup when the cup is in a relaxed or non-suction condition so that initial contact with the patient's skin is made at the peripheral rim of the cup and, following evacuation of the channel in the cup by said suction pump, the electrode plate of said first electrode makes contact with the patient's skin to obtain a signal at the skin surface responsive to a varying condition of the patient; and said cup having a resilience and form such that, when in contact with a patient's skin and subjected to suction, the wall of the cup deforms allowing the first electrode to be drawn down onto the patient's skin to make the required contact therewith, the peripheral rim and the centrally located mounting each have a respective lip projecting inwardly of the channel to provide the channel with an undercut configuration in cross-section into which the skin is drawn by the suction created within the channel, the oppositely directed lips acting to entrap the drawn in skin surface thereby enhancing the security of attachment of the suction cup.

* * * * *